United States Patent
Lamb

(10) Patent No.: US 6,806,251 B2
(45) Date of Patent: Oct. 19, 2004

(54) METHOD OF TREATING PAIN

(75) Inventor: Gregory Blair Lamb, Mississauga (CA)

(73) Assignee: 1474791 Ontario Limited, Ontario (CA)

( * ) Notice: Subject to any disclaimer, the term of this patent is extended or adjusted under 35 U.S.C. 154(b) by 0 days.

(21) Appl. No.: 10/062,954

(22) Filed: Jan. 31, 2002

(65) Prior Publication Data

US 2003/0143249 A1 Jul. 31, 2003

(51) Int. Cl.$^7$ .................. A61K 38/00; A61K 39/08; A61K 38/16; C07K 14/00
(52) U.S. Cl. .................. 514/2; 424/247.1; 530/350; 128/907
(58) Field of Search .................. 424/234.1, 236.1, 424/239.1, 247.1, 143.1; 514/2, 184.1; 530/300, 35, 350; 128/907

(56) References Cited

U.S. PATENT DOCUMENTS

| | | | | |
|---|---|---|---|---|
| 3,903,301 A | * | 9/1975 | Share | .................. 514/603 |
| 5,053,005 A | | 10/1991 | Borodic | |
| 5,054,486 A | * | 10/1991 | Yamada | .................. 607/3 |
| 5,766,605 A | | 6/1998 | Sanders et al. | |
| 5,989,545 A | | 11/1999 | Foster et al. | |
| 6,037,373 A | * | 3/2000 | De Simone | .................. 514/556 |
| 6,113,915 A | | 9/2000 | Aoki et al. | |
| 6,235,289 B1 | | 5/2001 | Aoki et al. | |
| 6,290,961 B1 | * | 9/2001 | Aoki et al. | .................. 424/184.1 |
| 6,500,436 B2 | * | 12/2002 | Donovan | .................. 424/239.1 |
| 2002/0032155 A1 | * | 3/2002 | Ferree | .................. 514/12 |

FOREIGN PATENT DOCUMENTS

WO  WO 00/15245  *  3/2000

OTHER PUBLICATIONS

Al–Khodairy et al., Spinal Cord, vol. 36, pp. 854–858 (1998).*
Borodic et al., Drug Safety, vol. 11(3), pp. 145–52 (1994).*
Rasmussen Ugesckrift for Laegar, 162(48): 6557–61 (Nov. 2000, with medline English abstract).*
Bajek et al., Acta Med Okayama vol. 54 No. 6, pp. 235–41 (2000).*
Yoshihara et al., Spine, vol. 26 No. 6, pp. 622–26 (2001).*
Dave Davis et al.; *Significant Improvement of Stiff–Person Syndrome After Paraspinal Injection of Botulinum Toxin A*; Movement Disorders: Official Journal of The Movement Disorder Society, USA; Jul. 1993; pp. 371–373; vol. 8, No. 3.
Leslie Foster et al.; *Botulinum toxin A and chronic lower back pain*; Neurology, USA, May 22, 2001; pp. 1290–1293; vol. 56, No. 10.
Cynthia L. Comella et al.; *Extensor Truncal Dystonia: Treatment With Botulinum Toxin Injections*; Movement Disorders: Official Journal of The Movement Disorder Society, USA; May 1998; pp. 552–555; vol. 13, No. 3.
Doris Burg et al.; *Effective treatment of a large muscle hernia by local botulinum toxin administration*; Handchir. Mikrochir. Plast. Chir.; Germany; Mar. 1999; pp. 75–78; vol. 31, No. 2.
Holger G. Gassner et al.; *Addition of an Anesthetic Agent to Enhance the Predictability of the Effects of Botulinum Toxin Type A Injections: A Randomized Controlled Study*; Mayo Clinic Proceedings; United States; Jul. 2000; pp. 701–704; vol. 75, No. 7.

* cited by examiner

Primary Examiner—James Housel
Assistant Examiner—Zachariah Lucas
(74) Attorney, Agent, or Firm—Summa & Allan, P.A.

(57) ABSTRACT

The invention provides a method for treatment of pain, the method comprising administering to the intrinsic spinal muscles of a mammal an amount of an agent sufficient to paralyze said muscles.

10 Claims, 2 Drawing Sheets

METHOD OF TREATING PAIN

FIELD OF THE INVENTION

The present invention is directed to the injection of a paralyzing agent into the intrinsic spinal muscles to treat chronic pain.

BACKGROUND OF THE INVENTION

Chronic pain may be generally described as any pain that persists beyond the usual course of a disease or beyond the reasonable time for an injury to heal. Chronic pain negatively impacts all aspects of an individual's life, including emotional, vocational, financial and social elements.

A very common type of chronic pain is back pain or spinal pain. The spine is a column of bone and cartilage that extends from the base of the skull to the pelvis. It encloses and protects the spinal cord and supports the trunk of the body and the head. The spine comprises approximately thirty-three vertebrae. A joint, which stabilizes the vertebral column and allows it to move, connects each pair of vertebrae. Between each pair of vertebrae is a disk-shaped pad of fibrous cartilage with a jelly-like core, which is called the intervertebral disk, or usually just the "disk". These disks cushion the vertebrae during movement.

There are deep spinal muscles surrounding the vertebrae and disks. These muscles are herein referred to as "intrinsic spinal muscles" because they are intrinsic or interwoven within the spine. Over time, or in response to injury, these muscles may become shortened and contribute to myofascial pain.

Many different therapies and products have been tried in the treatment of chronic pain. One promising product, called Botox™, is a commercial product based on botulinum toxin. Botulinum toxin is produced by the bacteria, *Clostridium botulinum*. When injected into a muscle, the toxin prevents the release of acetylcholine and thus the muscle cannot contract.

U.S. Pat. No. 5,766,605 describes the use of botulinum toxin to control autonomic nerve function in a mammal. It has been found useful for conditions such as rhinorrhea, excessive salivation, asthma and excessive sweating.

U.S. Pat. No. 5,989,545 discloses Clostridial toxin derivatives which are able to modify peripheral sensory afferent functions. A targeting moiety is coupled to the toxin to direct the toxin and reduce side effects.

U.S. Pat. Nos. 6,113,915 and 6,235,289 are directed to methods of treating pain by intrathecal administration of botulinum toxin type A. The toxin is administered to the intrathecal space between the arachnoid membrane and the pia mater.

Although the use of botulinum toxin in the treatment of chronic pain is known, there can be serious side effects associated with the known methods of use. Unless the toxin is very specifically delivered to a particular muscle, there can be diffusion effects. Botulinum toxin is a very powerful paralytic poison and naturally the more that is administered to allow sufficient binding to the muscle, the greater the risk of inappropriate paralysis. The toxin's effect generally lasts about three months and is not reversible. For example, the use of Botulinum toxin for the treatment of facial lines has sometimes had the undesirable effect of facial or eyelid drooping, or lack of control of important muscles for smiling, etc. Thus, it is clearly apparent that if Botulinum toxin is to be used in the spinal area to treat chronic pain, new and improved methods are required.

SUMMARY OF THE INVENTION

The present invention is directed to a novel method for treating pain using botulinum toxin. Particularly, it applies to the application of Botulinum toxin to treat herniated disks, spinal neuropathy, compressed and degenerated disks of the spine, and facet joint disease of the spine as caused by intrinsic spinal muscle dysfunction, and the complications thereof. The method is generally referred to as specific deep paraspinal paralysis.

In one aspect, the method of the present invention comprises administering to the intrinsic spinal muscles of a mammal an amount of a toxin sufficient to paralyze the muscles. This prevents the muscles from shortening and can allow healing to occur.

In a preferred embodiment, the toxin is botulinum toxin type A. The toxin may be administered as a single dose or in a number of injections.

In another aspect, the present invention provides for the use of botulinum toxin as an agent for the injection of an intrinsic spinal muscle.

In a further aspect of the invention, a paralyzing agent is used in combination with a growth factor to treat spinal compression.

In yet another aspect of the invention, a kit for the treatment of pain by injection of the intrinsic spinal muscles is provided. The kit comprises:
 a) a paralyzing agent;
 b) an injection syringe with needle; and
 c) an acupuncture needle with injector system.
In a preferred embodiment the kit comprises:
 a) botulinum toxin;
 b) saline for diluting the toxin;
 c) a syringe with needle for dispensing the saline into the toxin;
 d) a spinal botulinum injection needle;
 e) an acupuncture needle with spinal acupuncture injector system; and
 f) at least one injection syringe.

Preferably the botulinum toxin is provided in a vial containing 25, 50, 75 or 100 units and the the acupunture needle is a 21/2"—50–60 mm acupuncture 0.25 mm gauge needle with injector system. The kit may also include a local anesthetic such as Naropin, Xylocaine or Marcaine or other local anesthetic. An instructional video for physicians demonstrating injection of intrinsic muscles in the cervical, thoracic or lumber areas may also be provided.

BRIEF DESCRIPTION OF THE DRAWINGS

Preferred embodiments of the invention are described below with reference to the drawings, wherein.

DETAILED DESCRIPTION

The present invention is directed to a novel method of treating chronic spinal pain and its complications. The method involves the injection of very low doses of Botulinum toxin or its equivalent into the intrinsic spinal muscles.

Figure 1:
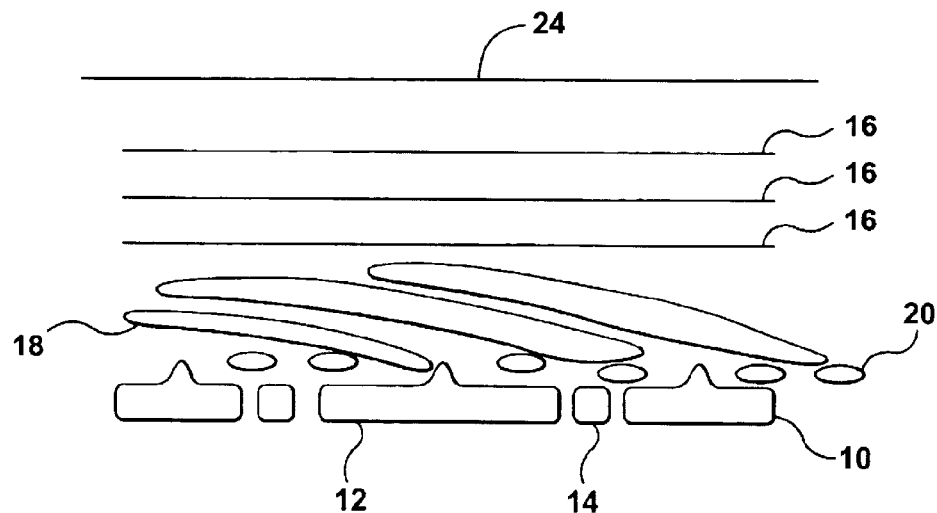
FIG. 1 is a side view of a segment of the spine illustrating the intrinsic musculature.

FIG. 1 is a side view of a segment of the spine illustrating the associated musculature. The spinal column 10 harbors and protects the spinal cord. The spinal column comprises vertebrae 12 and disks 14. The spine is lined with five layers of muscles. The three top layers 16 are designed to be the heavy work muscles for the spine and the two deepest layers are designed to provide structural integrity to the spine. The second deepest layer of muscles is the mutifidus 18. The multifidus plays a major role as a segmental stabilizer. The deepest set of muscles are the rotator brevis and longus 20. In combination, these deep muscles, which comprise primarily the multifidus and the rotator brevis and longus muscles, support the spine and allow it to move without falling apart. The multifidus 18 and rotator 20 muscles, referred to herein as the intrinsic muscles, are very strong but also very small.

The present invention is based on the concept that injury over time can cause the deep/intrinsic muscles to become very tight and scarred, which, in turn, causes compression of the spine. The deep muscles likely contribute to many cases of spinal pain, yet very few treatments have been developed involving these muscles due to the fact that they are very small and difficult to manipulate. The present invention discloses a method of specifically treating these muscles thereby enabling the spine to relax and healing to occur.

Figure 2:
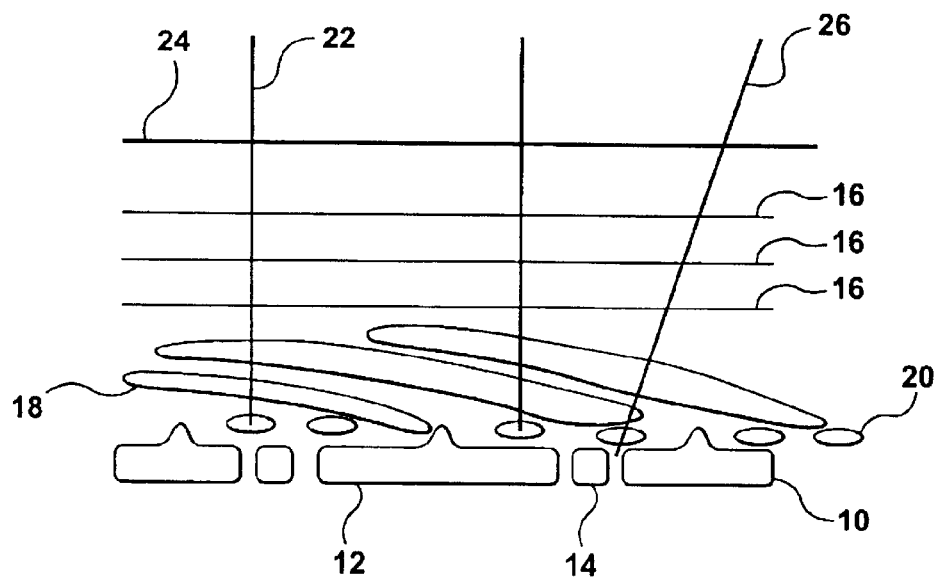
FIG. 2 is a side view of a segment of the spine indicating the sites for injection.

Referring now to FIG. 2, we can see how the rotator muscles can be injected with an agent such a botulinum toxin. The agent may be provided in liquid or dry form. The dry form is typically dissolved in saline to the appropriate dilution. In a preferred embodiment, a vial of Botox™ containing 100 units (MU) is diluted with 4 of normal saline. This results in a concentration of 25 MU/ml.It is clearly apparent that other formats could be used to achieve the same result. Stronger or weaker dilutions may be preferred depending on the volume to be injected and the degree of paralysis necessary.

The diluted agent is then drawn onto an injection syringe fitted with an injection needle 22. The injection needle 22 should be of a length sufficient to penetrate the distance through the skin 24 and upper three layers of muscles 16. This distance is generally in the range of 40 to 80 mm. Preferably, a 60 mm. injection needle is used. The placement of the needle 22 must be very specific to achieve the advantageous effects of the present invention.

In a preferred method, the skin 24 is first penetrated with an acupuncture needle 26 to prepare the intrinsic muscles for injection. The acupuncture needle 26 is directed away from the midline and between the vertebrae. Preferably, the acupuncture needle 26 penetrates the skin 24 approximately 5 to 7.5 mm away from the midline, medially and centrally and in between the transverse processes of the superior and inferior vertebrae. A gradual but persistent downward pressure with a turning motion, left to right, is then applied to the acupuncture injector handle to allow gradual penetration into the superficial and deep intrinsic spinal muscles. This causes a release of the spinal scar and spasm.

This manipulation prepares the deep spinal muscle for the botulinum toxin injection. The mechanical release may be done immediately before botulinum toxin Injection, or 1 to 14 days before botulinum toxin injection. The mechanical release is a preferable, but not essential step, of the method. Once a sufficient mechanical release is achieved, the injection syringe 22 containing the botulinum toxin is introduced in a similar manner as the acupuncture needle 26 until the multifidus muscles 18 and rotator brevis and longus muscles 20 are reached. Once the injecting needle 22 penetrates these muscles, the botulinum toxin is injected into the multifidus 18 and rotator brevis and longus muscles 20. The typical required dose ranges from about 1 to 20 MU of Botulinum toxin for each neurological level (i.e. L3 to L4). Preferably, 2 to 10 MU and most preferably, 4 to 8 MU of botulinum toxin are injected per level. It is clearly apparent that occasionally a higher dose may be required, and occasionally a lower dose may be required. Follow-up injections 2 to 12 weeks after the primary treatment may sometimes be performed.

The method of the present invention may be applied at any neurological level. The injection causes the multifidus muscle 18 and rotator brevis and longus muscles 20 to relax, despite their propensity for reoccurring spasm. This facilitates decompression of the vertebral segments at the injection sites. The vertebrae 12 and the disks 14 can decompress. This, in turn, allows the canals through which the dorsal nerve roots travel to become unimpinged. This leads to a reduction of neuropathy and radiculopathy and their complications and side effects.

In the case of lumbar radiculopathy of the L3 or L4 or L5 or S1 nerve roots, these nerve roots will begin to transmit normal or increased levels of conduction of information and neuroelectrical activity. This results in a reduction in pain and the resumption of normal functioning of the affected limb, such as an arm or leg. In the case of an arm, the levels most commonly treated would be from C4 to T6. In a case of a leg radiculopathy, the most common locations for reversal would be T10 to S2. The most common locations in the neck and low back are between C5 to C7 and L3 to S1, respectively. However, given the utility of the method of the present invention with respect to other pain syndromes, some of which have been mentioned above, virtually all vertebral segments are potentially injectable with Botulinum toxin within the multifidus and rotator brevis and longus muscles.

Biophysically, the base of the neck and the lower back are the most susceptible to injury and scarring. The region between the fifth and seventh cervical vertebrae are preferred sites in the cervical region. In the lower back, the preferred sites are between the fourth lumbar vertebrae and the first sacral vertebra. It should be understood, however, that the method of the present invention can be applied at virtually all levels of the spine, depending on the particular situation.

In the present invention, unlike previously known methods, the Botulinum toxin is injected directly into the deep muscles surrounding and supporting the spine rather than into the spaces between the meningeal sheaths. This provides the surprising result that very low doses can be used with great efficacy and few side effects. Because the Botulinum toxin is injected directly into the muscle, there is greater specificity and the risk of diffusion is minimized. Furthermore, because specific muscles are targeted, a lower dose can be used to achieve a therapeutic effect.

Figure 3:
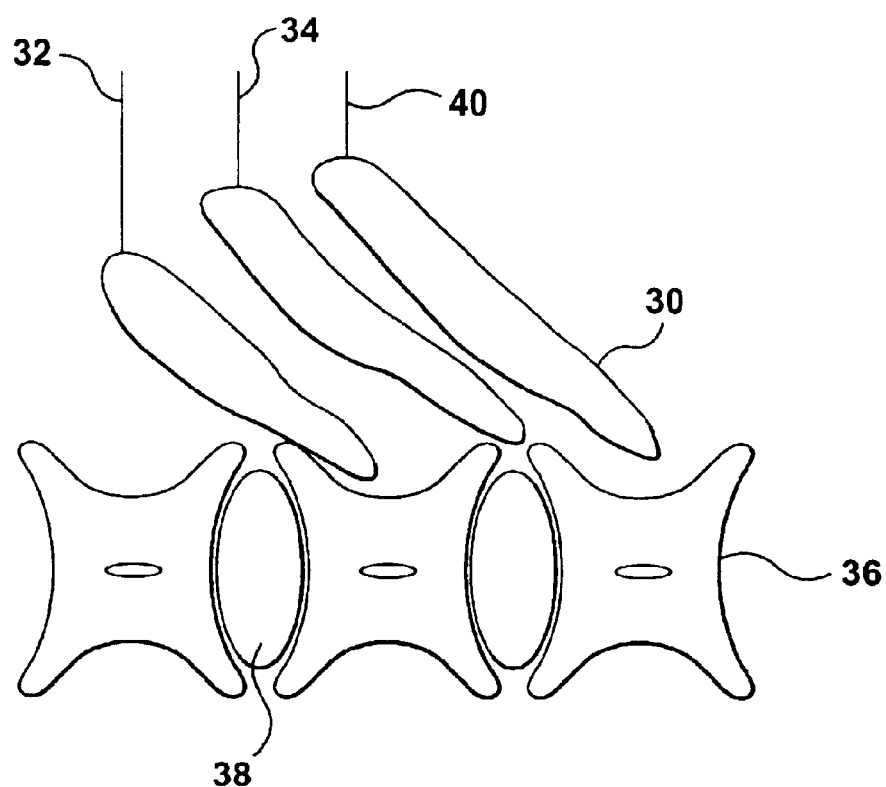
FIG. 3 is a top view of a segment of the spine illustrating injection with more than one agent.

In the method of the present invention, other factors which promote tissue regeneration of bone, disk, facet joints, muscles, cartilage and ligaments may also be administered to the deep spinal muscles, either alone or in combination with botulinum toxin or another muscle relaxant. In one preferred embodiment, illustrated in FIG. 3, the mutifidis muscles 30 are first injected with an acupuncture needle 32 to release the scars. An injection needle 34 is then used to administer Botulinum toxin to the multifidus 30 thereby promoting muscle relaxation which allows the vetebrae 36 and the disks 38 to decompress. Then a tissue healing agent, such as human growth hormone, is injected via another needle 40 or via the same needle as the botulinum toxin. It is clearly apparent that agents, other than botulinum toxin, may be used to relax the intrinsic muscles. It is also clearly apparent that growth factors other than human growth hormone can be used in the method of the present invention. Examples of such growth factors include nerve growth factor (NGF), epidermal cell growth facto (EGF), transforming growth factor (TGF), platelet derived growth factor (PDGF), insulin-like growth factor (IGF), fibroblast growth factor (FGF) and bone morphogenic protein (BMF) as well as many others.

Deep paraspinal Botulinum toxin injected into the intrinsic muscles is useful in the treatment of syndromes such as disk herniation, facet joint disease of the spine, spinal stenosis, degenerated disks of the spine including the cervical, thoracic and lumbosacral spine and myofascial compression/traction neuropathies of the spine, and complications thereof.

Some of the conditions associated with myofascial compression neuropathies include migraine headaches, temporomandibular joint disease, tinnitus, vertigo, sciatica, radiculopathy, carpal tunnel syndrome, ulnar neuritis, tennis elbow, golfers elbow, RSI, rotator cuff injury, heartburn and reflux.

In addition to the method of the present invention, a kit is provided for performing a preferred embodiment of the method. The kit includes a set of materials to perform the method of the present invention. The kit comprises:

a) a paralysing agent such as botulinum toxin;

b) at least one injection syringe with needle; and c) an acupuncture needle with spinal injector system.

The kit may also include saline for diluting the paralysing agent. A local anesthetic is also optionally included. The kit may also further include a tissue repair agent. An instructional video may also be included.

In one preferred embodiment, a Botulinum Toxin Spinal Kit is provided which includes:

Frozen Botulinum Toxin vial or glass containing 25, 50, 75 or 100 units (botulism toxin composed of one of, or parts of, or combinations of chains A to G, typically botulinum toxin A) depending on kit A, B, C, or D.

1 or 2-Saline syringes/or local anesthetics (generally without preservative) Naropin, Xylocaine, Marcaine (saline syringe 1 or 2) of 10 ml in plastic or glass with rubber stopper. Each saline syringe has markings for every 0.5 cc/ml.

1 or 2-Needles 20–25 gauge (saline needle 1 or 2) to be attached to saline syringe for injecting sterilized saline of syringe directly into botulinum vial of A,B,C, or D Botulinum withdrawal needle 20–25 gauge 25–40 mm/1–1½"

2–2½"—50–60 mm spinal botulinum injection needle, 20–25 gauge

2–2½"—50–60 mm acupuncture 0.25 mm gauge needle with spinal acupuncture injector system 6-Injection syringes of 1–4 cc/ml with markings delineating dose line separations every 0.5 cc/ml for 1 cc/ml syringe Instructional (for physicians) video for spinal injection of cervical thoracic or lumber areas.

The present invention provides several surprising advantages over previous methods involving Botulinum toxin. A major difference between this particular procedure and other procedures involving the injection of botulism toxin is that this procedure specifically targets the deep spinal muscles multifidus and rotator brevis and longus. This targeting allows decompression of the specific vertebral segments surrounded by these paraspinal muscles. The result is the reversal of compression at the vertebral segments around which are injected by Botulinum toxin. This leads to a decrease in local or referred pain syndromes caused by chronic pain from the intrinsic muscles of the spine either directly or indirectly. This form of injection is effective in the area of the cervical, thoracic and lumbar spine. This type of injection can also be applied to the cervical, thoracic and lumbar spine to reverse patients with herniated disks in the lumbar spine.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

A young male, 40 years old, presented with low back pain, sciatica, radiculopaths, compression neuropathy. The patient had a 2 year history of severe sciatica in right leg and severe low back pain. A CT scan demonstrated 2 herniated disks of the lumbar spine and spinal stenosis of the right lumbar spine causing compression of the L5 and S1 nerve roots on the right. Reversal of spasm of the multifidus and rotator brevis muscles of the lower lumbar spine was achieved by injecting 4–6 mouse units of Botulism toxin into the muscles at L4 to S1. Two weeks later, there was an almost complete reversal of the disk herniation and sciatica as the botulinum toxin began working. Three months later, there were no symptoms of back pain or nerve root impingement. There were still no symptoms at six months, demonstrating an effect beyond the direct paralyzing botulinum toxin effect, indicating that a long term cure could be achieved.

Example 2

A thirty-three year old female had severe left back pain and sciatica for nine months. The patient was unable to walk, sit or lay flat on her back. She could lie only on the right side. The patient was treated using the present method with botulinum toxin and acupuncture into the intrinsic spinal muscles at L3-S1. Within 3–4 weeks, the patient had decreased back and left leg symptoms. By 8 weeks, patient was largely recovered and able to return to work. 6 months later, the patient had no symptoms on the left leg sciatica.

Example 3

A fifty year old male with three year history of reflux, heartburn and irritable bowel syndrome (IBS) had been treated with antacid medication with little success. The patient was treated with botulinum toxin injected at T5-10 bilaterally at a dose of 4 mouse units per location. Two weeks later, the patient had a lessening of stiffness of the thoracic spine and the heartburn symptoms and reflux symptoms had improved. By four weeks all symptoms of reflux and heartburn had ceased and the irritable bowel symptoms had also greatly decreased. The symptoms remained improved beyond 3 months and well into 6 months indicating long-term success with intrinsic spinal muscle relaxation.

Example 4

A thirty-eight year old female with left rotator cuff (suprasinatus) dysfunction and pain also had greatly reduced flexion of the left shoulder and also complained of intermittent upper back pain. The range of motion was reduced to only 70 degrees versus a normal range of 180 degrees. The patient was treated using intrinsic spinal botulinum toxin toxin in the multifidus, rotator brevis and longus. 2–4 mouse units of Botulinum toxin toxin were injected at T1–5 of the left thoracic spine and 1–2 mouse units on the right side of the each location of T1–5. By 2 weeks, the patient had less upper back pain and the shoulder was much less painful. By 4 weeks, the patient had much improved range of motion of left shoulder to 170 degree. The right side was also injected to provide "balance" to the upper thoracic spine.

Example 5

A twenty-eight year old female computer operator presented with with RSI, carpel tunnel, ulnar neuritis, tennis and golfer's elbow and temporal headaches. The patient has also been involved in a motor vehicle accident 2 years prior with whiplash. The patient was diagnosed 1 year ago with carpel tunnel syndrome bilaterally. Intrinsic spinal muscle lesions at C4 to T1, bilaterally involving the multifidus and rotator brevis and longus were suspected. The patient was treated with botulinum toxin injections of 2–4 mouse units bilaterally at C4-T1. Two weeks later the headaches had diminished. At 3 weeks the carpel tunnel, ulnar neuritis, tennis elbow and golfer's elbow had improved. The symptoms remained better beyond 6 months.

Example 6

A fifty-five year old male had developed frontal headache and chronic sinus pressure due to allergies and sleep apnea and also complained of moderate jaw pain (TMJ). The patient had a history of neck pain at the top of the neck. The patient was injected with 2–4 mouse units of botulinum toxin into the intrinsic muscles at C1 to C3 bilaterally. Two to three weeks later, the patient the headaches and jaw pain had resolved and the allergies had completely subsided. Snoring and sleep apnea were also reduced.

I claim:

1. A method of treating a disorder associated with spinal compression comprising administering an effective dose of botulinum toxin directly and solely to the intrinsic muscles of a patient in need of such therapy.

2. A method according to claim 1, wherein said disorder associated with spinal compression is selected from the group consisting of compression neuropathies, facet joint disease of the spin, sciatica, disc herniation, and degenerated discs.

3. A method according to claim 2, wherein the disorder is disc herniation or degenerated discs.

4. A method according to claim 1, wherein said botulinum toxin paralyzing agent is botulinum toxin A.

5. A method according to claim 1, wherein said toxin is administered in a dose between 1 and 30 mouse units of toxin per injection site.

6. A method according to claim 1, wherein said toxin is administered in a single injection.

7. A method according to claim 1, wherein said toxin is administered via a plurality of injections.

8. A method according to claim 3, further comprising the administration of a factor selected to enhance healing of the disc.

9. A method according to claim 8, wherein the factor is selected from the group consisting of human growth factor (HGF), nerve growth factor (NGF), epidermal growth factor (EGF), transforming growth factor (TGF), platelet derived growth factor (PDGF), insulin-like growth factor (IGF), fibroblast growth factor (FGF), and bone morphogenic protein (BMF).

10. A method of treating spinal compression comprising penetrating the skin with an acupuncture needle, advancing the acupuncture needle between two vertebrae to provide a mechanical release of the spinal muscles, introducing an injection syringe containing botulinum toxin, and injecting the toxin directly and solely into the intrinsic muscles.

* * * * *